US005679264A

United States Patent [19]
Gsell

[11] Patent Number: 5,679,264
[45] Date of Patent: *Oct. 21, 1997

[54] GAS PLASMA TREATED POROUS MEDIUM AND METHOD OF SEPARATION USING SAME

[75] Inventor: Thomas Charles Gsell, Glen Cove, N.Y.

[73] Assignee: PALL Corporation, East Hills, N.Y.

[*] Notice: The term of this patent shall not extend beyond the expiration date of Pat. No. 5,443,743.

[21] Appl. No.: 458,846

[22] Filed: Jun. 2, 1995

Related U.S. Application Data

[63] Continuation of Ser. No. 252,044, May 31, 1994, Pat. No. 5,443,743, which is a continuation of Ser. No. 990,794, Dec. 10, 1992, abandoned, which is a continuation of Ser. No. 757,535, Sep. 11, 1991, abandoned.

[51] Int. Cl.$^6$ .................... B01D 37/00; B01D 37/02; B01D 46/00; B05D 3/04
[52] U.S. Cl. ................. 210/767; 95/241; 95/273; 210/188; 210/503; 210/508; 210/649; 427/243; 427/244; 427/535; 427/536; 427/538; 427/539
[58] Field of Search .................... 210/654, 748, 210/767, 485, 488, 491, 496, 500.34, 500.35, 649, 500.36, 500.38, 500.41, 502.1, 188, 503, 508; 204/165, 168, 170; 427/535, 536, 538, 539, 244, 243; 428/409; 604/4, 5; 95/214, 241, 273; 55/527

[56] References Cited

U.S. PATENT DOCUMENTS

| | | |
|---|---|---|
| 3,065,157 | 11/1962 | Busse . |
| 3,107,206 | 10/1963 | Cottet et al. . |
| 3,188,165 | 6/1965 | Magat et al. . |
| 3,383,163 | 5/1968 | Menashi . |
| 3,870,610 | 3/1975 | Baird et al. ............... 204/165 |
| 4,072,769 | 2/1978 | Lidel . |
| 4,107,049 | 8/1978 | Sano et al. ............... 210/490 |
| 4,188,426 | 2/1980 | Auerbach . |
| 4,214,014 | 7/1980 | Hofer et al. . |
| 4,261,806 | 4/1981 | Asai et al. ............... 204/165 |
| 4,411,866 | 10/1983 | Kanno ............... 422/25 |
| 4,445,991 | 5/1984 | Arbit ............... 204/168 |
| 4,483,694 | 11/1984 | Takamura et al. . |
| 4,488,954 | 12/1984 | Hatada et al. ............... 204/169 |
| 4,503,133 | 3/1985 | Van Lier et al. ............... 429/174 |
| 4,504,349 | 3/1985 | Ueno et al. . |
| 4,508,781 | 4/1985 | Yagi et al. ............... 428/409 |
| 4,548,867 | 10/1985 | Ueno et al. . |
| 4,572,724 | 2/1986 | Rosenberg et al. ............... 210/436 |
| 4,606,930 | 8/1986 | Ueno et al. . |
| 4,613,517 | 9/1986 | Williams et al. ............... 427/2 |
| 4,656,083 | 4/1987 | Hoffman et al. ............... 428/265 |
| 4,686,149 | 8/1987 | Aonuma et al. ............... 428/522 |
| 4,824,444 | 4/1989 | Nomura . |
| 4,845,132 | 7/1989 | Masuoka et al. . |
| 4,861,617 | 8/1989 | Pall et al. ............... 427/508 |
| 4,880,548 | 11/1989 | Pall et al. ............... 210/508 |
| 4,933,092 | 6/1990 | Aunet et al. ............... 210/638 |
| 4,948,628 | 8/1990 | Montgomery et al. . |
| 4,954,256 | 9/1990 | Degen et al. ............... 210/490 |
| 5,028,332 | 7/1991 | Ohnishi ............... 210/500.34 |
| 5,041,304 | 8/1991 | Kusano et al. . |
| 5,112,690 | 5/1992 | Cohen et al. . |
| 5,198,263 | 3/1993 | Stafford et al. ............... 427/577 |
| 5,217,627 | 6/1993 | Pall et al. ............... 210/767 |
| 5,232,600 | 8/1993 | Degen et al. ............... 210/640 |
| 5,234,723 | 8/1993 | Babacz ............... 427/491 |
| 5,258,127 | 11/1993 | Gsell et al. ............... 210/767 |
| 5,282,965 | 2/1994 | Urairi et al. ............... 210/500.36 |
| 5,409,696 | 4/1995 | Narayanan et al. ............... 210/500.24 |
| 5,437,900 | 8/1995 | Kuzowski ............... 210/510.1 |
| 5,443,743 | 8/1995 | Gsell ............... 210/767 |
| 5,451,321 | 9/1995 | Matkovich ............... 210/641 |

FOREIGN PATENT DOCUMENTS

| | | |
|---|---|---|
| 267286 | 5/1988 | European Pat. Off. . |
| 1256971 | 10/1989 | Japan . |

OTHER PUBLICATIONS d'Agostino, Riccardo, "Plasma Deposition, Treatment, & Etching of Polymers", Plasma—Materials Interactions, 1990, pp. 463–516.

*Primary Examiner*—John Kim
*Attorney, Agent, or Firm*—Leydig, Voit & Mayer, Ltd.

[57] ABSTRACT

A gas plasma treated porous medium and method of using such a medium to separate or remove materials such as components of biological fluids.

16 Claims, No Drawings

GAS PLASMA TREATED POROUS MEDIUM AND METHOD OF SEPARATION USING SAME

This is a continuation patent application of prior patent application Ser. No. 08/252,044, filed May 31, 1994, now U.S. Pat. No. 5,443,743, which is a continuation of Ser. No. 07/990,794, filed Dec. 10, 1992, abandoned, which is a continuation of Ser. No. 07/757,535, filed on Sep. 11, 1991, which is now abandoned.

TECHNICAL FIELD

This invention relates to a gas plasma treated porous medium and the use of such a porous medium to separate or remove materials, particularly components of biological fluids such as blood.

BACKGROUND OF THE INVENTION

Many materials, particularly fluids, are passed through porous media to separate or remove certain materials. In particular, biological fluids, containing a variety of components and constituents, are typically passed through porous media for such purposes. For example, it is sometimes desirable to separate whole blood into one or more component parts and/or to remove a cellular constituent such as leucocytes from whole blood or a blood component. Thus, improved porous media and separation techniques are desirable to separate and/or remove a component or constituent from a fluid.

The depletion of deleterious matter in biological fluids administered to a patient for therapeutic reasons is of considerable importance to avoid potential harmful effects on the recipient of the fluid. Of particular importance is the depletion of deleterious matter, especially leucocytes, from biological fluids such as blood and blood products used in transfusions and in extracorporeal circuits to prevent or reduce reperfusion injury, as well as a number of other diseases and conditions.

It has been the practice for many years to transfuse whole blood, and more recently blood components, from one or more donors to other persons. With the passage of time and the accumulation of research and clinical data, transfusion practices have improved greatly. One aspect of current practice is that whole blood is rarely administered; rather, patients needing red blood cells are given packed red cells (hereinafter PRC), and patients needing platelets are given platelet concentrate (hereinafter PC). These components are typically separated from whole blood by centrifuging, the process providing, as a third product, plasma, from which various other useful components are obtained.

In addition to the three above-listed components, whole blood contains white blood cells (known collectively as leucocytes) of various types, of which the most important are granulocytes and lymphocytes. In the donor, white blood cells provide protection against bacterial and viral infection.

However, the transfusion of any leucocyte—containing fluid, such as packed red cells or whole blood containing donor leucocytes may be harmful to the recipient. Some of the viral diseases induced by transfusion therapy, e.g., Cytomegaloviral Inclusion Disease, which is a life threatening infection to newborns and debilitated adults, are transmitted by the infusion of homologous leucocytes. Another life-threatening phenomenon affecting immunocompromised patients is Graft versus host disease (GVH), a disease in which the transfused leucocytes actually cause irreversible damage to the blood recipient's organs as well as the skin, gastrointestinal tract and neurological system. In this clinical syndrome, donor lymphocytes transfused with the platelet preparations can launch an immunological reaction against the host, i.e. the transfusion recipient, with pathological consequences. Conventional red cell transfusions have also been indicted as adversely influencing the survival of patients undergoing surgery for malignancy of the large intestine. It is believed that this adverse effect is mediated by the transfusion of agents other than donor red blood cells, including the donor's leucocytes.

The transfusion of platelet concentrate is also not without risk for those patients receiving both acute and chronic transfusion support. Chills, fever and allergic reactions may occur in patients receiving acute as well as chronic platelet therapy. Repeated platelet transfusions frequently leads to alloimmunization against HLA antigens, as well as platelet specific antigens. This in turn decreases responsiveness to platelet transfusion. Leucocytes contaminating platelet concentrates, including granulocytes and lymphocytes, are associated with both febrile reactions and alloimmunization leading to platelet transfusion refractoriness. Another potential consequence of platelet transfusion is the transmission of bacterial, viral, and parasitic infectious diseases.

In the currently used centrifugal methods for separating blood into the three basic fractions (packed red cells, platelet concentrate, and plasma), the leucocytes are present in substantial quantities in both the packed red cells and platelet concentrate fractions. It is generally accepted that it would be highly desirable to reduce the leucocyte concentration of these blood components to as low a level as possible. While there is no firm criterion, it is generally accepted that many of the undesirable effects of transfusion would be reduced if the leucocyte content were reduced by a factor of about 100 or more prior to administration to the patient. This approximates reducing the total content of leucocytes in a single unit of PRC (the quantity of PRC obtained from a single blood donation) to less than about $1 \times 10^7$. Recently it has become more widely perceived that in order to prevent viral infection by transfused blood, factors of reduction should be more than 100, preferably more than 1000, and more preferably 30,000 or 100,000 fold or more, such as 1,000,000 fold.

One of the most effective means of reducing leucocyte content is disclosed in U.S. Pat. No. 4,925,572, which is directed towards the bedside filtration of PRC.

Accordingly, it is a primary object of the present invention to provide a separatory or removal porous medium through which a fluid, particularly a biological fluid, may be passed. It is another object of the invention to provide a porous medium capable of depleting deleterious matter from biological fluids. It is a further object of the invention to provide a porous medium that is capable of depleting leucocytes from blood and blood products. It is a more specific object of this invention to provide a porous medium that has been treated with a gas plasma to improve the ability of the medium to deplete deleterious matter, especially leucocytes (and more specifically granulocytic neutrophils), from biological fluids such as blood and blood products. Another object of the invention is to provide a porous medium which allows the passage of a significant amount of platelets therethrough. These and other objects and advantages of the present invention will become apparent to those skilled in the art in view of the following detailed description.

SUMMARY OF THE INVENTION

The present invention comprises a porous medium which has been gas plasma treated and its use in separating or removing substances from fluids. In particular, the present invention provides for a porous medium and method for the separation or depletion of deleterious matter from a biological fluid. For example, it has been found, unexpectedly, that a porous medium treated with gas plasma is especially beneficial for the depletion of leucocytes from blood and blood products. A significant and novel feature of this invention is that such a porous medium achieves high efficiency and capacity for leucocyte removal while minimizing loss of platelets.

The porous medium of the present invention is advantageous for several reasons. The leucocyte depletion capability of the porous medium is improved. Further, the gas plasma treated fibers have a relatively low adhesiveness to platelets so that the ability of the porous medium to pass platelets therethrough is enhanced. Additionally, it is significantly more efficient to prepare the fibers in accordance with the present invention than it is to prepare fibers using other surface modification protocols since organic reagents are not used in the preparation of fibers modified by gas plasma and there is no need to wash or dry the fibers to remove extractables prior to use.

The present invention also provides a method for removing deleterious matter, such as leucocytes, from biological fluids such as blood. The method generally comprises depleting the content of deleterious matter from biological fluids by passing the fluid through a porous medium that has been treated with gas plasma.

DETAILED DESCRIPTION OF THE PREFERRED EMBODIMENTS

The present invention comprises a porous medium for separating or removing a component of a fluid, which porous medium has been treated with a gas plasma. The present invention also concerns a method of using such a gas plasma treated porous medium to separate or remove materials from fluids. The present invention is particularly useful in separating or removing deleterious matter such as leucocytes from biological fluids such as blood while allowing other desirable matter such as platelets to pass through the porous medium in significant amounts.

The porous medium of this invention may be formed by any suitable means of any suitable material which will be modified by treatment with gas plasma. For example, the present inventive porous medium may be formed of natural or synthetic fibers, cast from resin solutions, or prepared from sintered powder media. Considerations of cost, convenience, flexibility, and ease of fabrication and control, point to fibers as a preferred starting material, particularly commercially available fibers and resins used to prepare fibers.

Synthetic resins from which fibers are prepared commercially and which are suitable for use in the subject invention include, but are not limited to, polyolefins, such as polyethylene, polypropylene and polymethylpentene; polyamides, such as nylon 6, nylon 610, nylon 10, nylon 11, nylon 12 and nylon 66; polyesters, such as polybutylene terephthalate and polyethylene terephthalate; polysulfones; polyaramides; acrylics; polyarylene oxides and sulfides; polymers and copolymers made from halogenated olefins, such as polyvinylfluoride and polyvinylidene fluoride; polymers and copolymers made from unsaturated nitriles, such as polyacrylonitriles; and cellulose acetate. Preferred polymers are polyolefins, polyesters and polyamides. The most preferred polymer is polybutylene terephthalate (PBT).

In accordance with the present invention, the porous medium is treated with a gas plasma, preferably a low temperature gas plasma, with or without deposition of a polymeric substance formed by the plasma or introduced into the plasma. The porous medium may be treated with a gas plasma at any suitable point in its manufacture. For example, the porous medium may be treated with a gas plasma after it has been formed into its desired shape, or the fibers which are used to make the porous medium may be treated with gas plasma prior to formation of the porous medium. It is likewise possible to treat with gas plasma a precursor to the final form of the porous medium, as, for example, where the porous medium is first formed into a sheet-like structure, and the sheet-like structure is thereafter pleated or the like to form the final configuration of the porous medium as it will be used in the device. It is preferred to treat the fiber surfaces with the gas plasma prior to formation of the porous medium.

The term "plasma" or "gas plasma" is used generally to describe the state of an ionized gas. A plasma consists of high energy charged ions (positive or negative), negatively charged electrons, and neutral species. As known in the art, a plasma may be generated by combustion, flames, physical shock, or, preferably, by electrical discharge, such as a corona or glow discharge. In radio frequency (RF) discharge, a substrate to be treated is placed in a vacuum chamber and gas at low pressure is bled into the system. An electromagnetic field is generated by subjecting the gas to a capacitive or inductive RF electrical discharge. The gas absorbs energy from the electromagnetic field and ionizes, producing high energy particles. The gas plasma, as used in the context of the present invention, is exposed to the porous medium, thereby modifying the properties of the porous medium to provide the porous medium with characteristics not possessed by the untreated porous medium, e.g., improving the biocompatibility of the porous medium.

For plasma treatment of the porous medium or precursor materials, typically the gas plasma treatment apparatus is evacuated by attaching a vacuum nozzle to a vacuum pump. Gas from a gas source is bled into the evacuated apparatus through the gas inbleed until the desired gas pressure differential across the conduit is obtained. An RF electromagnetic field is generated in the plasma zone by applying current of the desired frequency to the electrodes from the RF generator. Ionization of the gas in the tube is induced by the field, and the resulting plasma in the tube modifies the fibers or medium in the plasma zone.

The gas used to treat the surface of the fiber or medium may include inorganic and organic gases used alone or in combination. Inorganic gases are exemplified by helium, argon, nitrogen, neon, nitrous oxide, nitrogen dioxide, oxygen, air, ammonia, carbon monoxide, carbon dioxide, hydrogen, chlorine, hydrogen chloride, bromine cyanide, sulfur dioxide, hydrogen sulfide, xenon, krypton, and the like. Organic gases are exemplified by acetylene, pyridine, gases of organosilane compounds and organopolysiloxane compounds, fluorocarbon compounds and the like. In addition, the gas may be a vaporized organic material, such as an ethylenic monomer to be plasma polymerized or deposited on the surface of the fiber. These gases may be used either singly or as a mixture of two or more of such gases according to need. The preferred gas according to the present invention is oxygen.

Typical parameters for the treatment of the porous medium or precursor materials with a gas plasma may include power levels from about 10 to about 3000 watts, preferably about 500 to about 2500 watts, and most preferably about 1500 to about 2500 watts; RF frequency of about 1 kHz to about 100 MHz, preferably about 15 kHz to about 60 MHz, most preferably about 30 kHz to about 50 kHz; exposure times of about 5 seconds to about 12 hours, preferably about 1 minute to about 2 hours, most preferably about 10 to about 30 minutes; gas pressures of about 0.001 to 100 torr, preferably about 0.01 to 1 torr, and most preferably about 0.1 to about 0.5 torr; and a gas flow rate of about 1–2000 standard cc/min.

The gas plasma treated porous medium of the present invention is useful in the separation and removal of materials in any type of gaseous or liquid fluid amenable to separation or removal techniques by passage through a porous medium. The present inventive porous medium is particularly useful for the separation and removal of substances in liquid fluids, especially biological fluids. Biological fluids include any treated or untreated fluid associated with living organisms, particularly blood, including whole blood, warm or cold blood, and stored or fresh blood; treated blood, such as blood diluted with a physiological solution, including but not limited to saline, nutrient, and/or anticoagulant solutions; one or more blood components, such as platelet concentrate, platelet-rich plasma, platelet-poor plasma, plasma, or packed red cells; analogous blood products derived from blood or a blood component or derived from bone marrow; and other leucocyte or leucocyte precursor cell-containing liquids.

Illustrative matters which may be separated from such biological fluids include deleterious matter such as activated and non-activated leucocytes (including neutrophils or granulocytic neutrophils), fat emboli, microaggregates, lipids, cells which are morphologically similar to leucocytes, cellular components and material, and other debris. Other matters which may be separated from biological fluids include cancer cells, stem cells, and the like.

The present inventive porous medium is particularly useful in the removal of deleterious matter, especially leucocytes, from biological fluids, such as blood and blood products. In addition, and unexpectedly, the gas plasma treated porous medium is capable of removing leucocytes from blood and blood products without removing a substantial quantity of the platelets therein, i.e., while allowing platelets to pass therethrough.

While the precise mechanism by which the gas plasma improves the characteristics of the porous medium to make them more suitable for the separation and removal of substances from fluids, particularly biological fluids, is not presently known, it is believed that the gas plasma modifies the surface characteristics of the porous medium, thereby affecting the interaction between the porous medium and the components of the fluid, e.g., platelets and leucocytes suspended in biological fluids such as blood and blood products. The exact nature of the surface modification is not fully understood at present. It has been observed, however, quite surprisingly and unexpectedly, that a porous medium made from fibers treated with gas plasma exhibits enhanced leucocyte depletion of blood and blood products and, beneficially, inhibited retention of platelets.

Factors which may affect the efficiency of the porous medium to separate or remove substance from fluids, particularly to deplete deleterious matter from biological fluids, and its utility for a given application, include, but are not limited to, the diameter of the fibers used to prepare the porous medium, the pore rating of the porous medium, the flow rate of the biological fluid through the porous medium, the flow area of the porous medium, the density of the fibers used to prepare the porous medium, and the voids volume of the porous medium. The various factors can be varied singly or in combination to provide a gas plasma treated porous medium that will be suitable for the particularly desired purpose.

In those uses where the adsorption of a material by the porous medium is the mechanism for the separation or removal of the material, as is believed to be the case with leucocyte removal, it is to be expected that finer fibers will have higher capacity and that the quantity as measured by weight of fibers necessary to achieve a desired efficiency will be less if the fibers used are smaller in diameter, since the surface area of a given weight of fibers is inversely proportional to the diameter of the fibers. For this reason, finer fibers, i.e., fibers with diameters as small as possible, are preferred for uses involving adsorption such as in leucocyte depletion.

While synthetic fibers made by conventional spinneret extrusion and drawing are not currently available smaller than about 6 micrometers in diameter, melt blowing, in which molten polymer is attenuated into fibers by a high velocity stream of gas and collected as a non-woven web is capable of making fibers on the order of a micrometer in diameter and has been essentially extended to the lower limit of fiber diameter with which coherent webs can be made. Webs with fiber diameters as small as about 1.5 to about 2 micrometers have been achieved, and even smaller diameter fibers can be made, but these are difficult to collect as a continuous web.

Some resins are better adapted to melt blowing of fine fibers than are others. Resins which work well include polyethylene, polypropylene, polymethylpentene, nylon 6, polyester PET (polyethylene terephthalate), and PBT (polybutylene terephthalate). Of the above-listed resins, PBT is preferred.

Other resins may be found which can be fiberized and collected as mats or webs with fibers as small as 1.5 micrometers or less, and such products, with their surfaces modified by gas plasma treatment, may be well suited to the fabrication of equally efficient porous media incorporating smaller fibers. Devices made using these or other fibers in the manner and for the purposes described in this invention should be understood to be within the scope of this invention.

While there is no upper limit to the average fiber diameter, practical considerations suggest an average fiber diameter in the range of up to about 40 µm, more likely about 10 to 15 µm, depending on the particular application. The lower limit of fiber diameter is the lower limit of average fiber diameter with which fibrous webs can be made. Fibers as fine as 0.2 µm diameter have been made and may be used in connection with the present invention.

The structure of the present inventive porous medium may be a multilayer structure wherein the layers are hot compressed by techniques known to those skilled in the art. The layers of such a porous medium may be bonded, fused, or otherwise fixed to one another, or they may simply be mechanically entwined. The porous medium may be configured in any way deemed desirable, for example, as a web, matrix, flat sheet, membrane, or in a corrugated or pleated structure.

The pores of the porous media of the present invention may have any pore diameter suited to the particular contemplated end use, such as, for example, leucocyte depletion from whole blood, packed red cells, platelet and platelet rich plasma. The term "pore diameter" as used herein is determined by the modified OSU FR test described in detail in U.S. Pat. No. 4,880,548. Generally, the pore diameter of the porous medium in accordance with the invention may be in the range of from about 0.5 μm to about 50 μm, preferably about 2 to 10 μm. Typically the pore diameter for leucocyte removal from packed red cells will be relatively smaller than the pore diameter of a porous medium used for leucocyte depletion from platelet rich plasma and for circulating blood in an extracorporeal circuit. A larger pore diameter, on the order of about 6 μm or so, may be used while still retaining desirable efficiency with satisfactory surface modification of the porous medium. The optimization of the pore size of the porous medium for a particular end use will be well understood by those skilled in the art.

Other factors which may affect the efficiency of the porous medium and its utility for a given application include, by way of illustration, and not in limitation of the invention, the weight of the fiber and the voids volume of the porous medium. For example, the efficiency of leucocyte removal will generally be enhanced by increasing the weight of the fiber and reducing the voids volume of the porous medium. Care, however, needs to be taken not to use a fiber diameter so small that the porous medium will collapse at normal working differential pressure. Similarly, the flow rate may be increased by increasing the area of the porous medium with a concomitant reduction in the thickness of the medium, or by increasing the voids volume of the porous medium.

When the porous medium is to be used for the leucocyte depletion of platelet-containing biological fluids, such as whole blood in an extracorporeal circuit, the porous medium is treated with gas plasma in such a fashion that the platelet loss by failure to pass through the porous medium may be minimized. The porous media of the present invention are thus capable of passing a significant portion of the platelets. Desirably, the porous media of the present invention are capable of passing at least about 40% of the platelets, more preferably at least about 50% of the platelets, and most preferably at least about 60% or more of the platelets.

It is generally desirable to include the porous medium of the present invention in a housing to contain the biological fluid. The housing is susceptible to a wide variety of shapes, and housings can, in turn, be designed to accept a variety of shapes of porous medium. For example, a circular, square, cylindrical, octagonal or the like housing designed to accommodate a similarly shaped porous medium would in principle all be functional, provided that adequate flow area is provided by the porous medium. These shapes are within the scope of the claimed invention. Accordingly, any housing of suitable configuration may be used.

The housing defines a liquid flow path from an inlet through the porous medium to an outlet. The housing may be fabricated from any sufficiently rigid, impervious material which is compatible with the biological fluid. For example, the housing may be fabricated from a metal, such as stainless steel, or from a polymer. Preferably, the housing is fabricated from a plastic material, such as polystyrene, polycarbonate, or polypropylene. In addition, all of the surfaces of the housing which contact the biological fluid are preferably liquophilic, i.e., readily wettable by the liquid. Internal surfaces of the housing may be treated to achieve a high degree of liquophilicity, e.g., by surface graft co-polymerization of hydroxyl functional monomers or by subjecting the internal surfaces to gas plasma treatment. These liquophilic internal surfaces then readily facilitate the release of gas bubbles during the preparation and priming operation. A method of reducing the adhesion of bubbles in medical equipment is disclosed in U.S. Pat. No. 4,861,617.

The housing may also be constructed of materials which have been exposed to a gas plasma in much the same manner as the porous medium. Such a gas plasma treated housing could, therefore, exhibit some of the same improved characteristics as the porous medium of the present invention, e.g., minimizing the retention of platelets in the separation or removal of blood components.

EXAMPLES

Example 1

A filter assembly in accordance with the invention was produced as follows: polybutylene terephthalate (PBT) was formed into fibers by melt blowing, i.e., exposing molten PBT resin to a high velocity stream of gas, until 7.5 gm/ft$^2$ (80.7 gm/m$^2$) of fibers having an average diameter of 2.0 microns was obtained. Four layers were formed over a layer of 40 micron opening woven polyester mesh. These five layers were pleated together with an extruded polypropylene mesh having a thickness of 0.02 inch (0.05 cm) and openings of about 0.06 inch (0.15 cm) by 0.06 inch (0.15 cm). The pleats were formed using conventional pleating equipment having heated platens to maintain the pleated structure to form a structure having 10 pleats per inch (2.54 cm) and a height of about 0.4 inch (1.02 cm).

The pleated media assembly was cut to a length of 2.5 inches (6.35 cm) and a width of 4 inches (10.16 cm), i.e., about 40 pleats. The assembly was formed into a cylindrical structure and the ends were sealed using a conventional heat sealer. The dimensions of the cylindrical pleated structure were about 1.4 inches (3.56 cm) inside diameter by 2.2 inches (5.59 cm) outside diameter by 2.5 inches (6.35 cm) length. A 1.3 inches (3.30 cm) outside diameter by 2.5 inches (6.35 cm) length polypropylene core was placed inside the pleated cylinder, and polypropylene end caps were heat welded to the ends of the cylinder.

The filter assembly was then subjected to gas plasma treatment by exposing the assembly, in a B-series gas plasma generator obtained from Advanced Plasma Systems, Inc., to an $O_2$ plasma under the following conditions: 2.0 kilowatts, 40 kilohertz for 20 minutes and 150 mtorr $O_2$. The filter assembly was then assembled into a housing in preparation for testing for leucocyte removal from blood.

Example 2

This Example illustrates the use of the gas plasma treated porous medium of Example 1 in an extracorporeal circuit for the removal of leucocytes from blood. This test was designed to expose recirculating blood to the conditions typical of those encountered during cardio-pulmonary bypass surgery: an extracorporeal circuit having a pump, filter, pressure gauge, and reservoir; a blood flow rate of 3–6 liters per minute was maintained throughout the test; and recirculating the blood for about three hours. Blood samples were taken and the differential pressure across the filter was measured at various times during the test.

Six units of type-matched packed red cells to which the anti-coagulant Adsol™ had been added were placed in the reservoir. After the filter and circuit were primed, blood in the reservoir was recirculated through the system at a flow rate of 3–6 liter per minute.

From samples of blood taken at various intervals during the test, it was found that the total leucocyte removal (neutrophils and lymphocytes), using a gas plasma treated porous medium produced as described in Example 1, was 39% after 1 hour of recirculation and 59% after 3 hours, the conclusion of the test. The pressure differential was less than 2 psi throughout the test.

By comparison a porous medium prepared with radiation grafted fibers and of the same construction as the gas plasma treated porous medium, leucocyte removal was 29% after 1 hour and 36% after 3 hours. These results illustrate the ability of the gas plasma treated porous medium of the present invention to remove a leucocytes effectively while maintaining a desirably low pressure drop.

Example 3

A web of melt blown PBT microfibers having an average fiber diameter of about 2.4 microns was prepared as described in Example 1. The PBT web was formed into a multilayered structure having a total of 52 grams/ft$^2$ of the above media. A PBT porous medium (untreated) having a final thickness of about 0.08 inch was formed by heating the multilayered structure to a temperature of about 170° C. and applying pressure.

A portion of the PBT porous medium (untreated) was subjected to treatment with gas plasma with oxygen using the following conditions: 40 kHz radio frequency at 2000 watts for 15 minutes. The oxygen ($O_2$) pressure was 115 mtorr. The gas plasma treated porous medium is referred to herein as the GPT porous medium. The remainder of the PBT porous medium (untreated) was used for comparative testing.

The GPT porous medium was then tested for platelet loss from both packed red cells and platelet concentrate. To carry out the testing, samples of the GPT porous medium were cut into a 0.94 inch diameter disc, and sealed in a reusable plastic housing. The housing included an inlet port and an outlet port and defined a liquid flow path between the inlet and the outlet through the GPT porous medium.

Test with Platelet Concentrate

Platelet concentrate pooled from random donors was passed through the GPT porous medium in the test housing described above at an initial flow rate of 1 cc per minute. The concentration of platelets and leucocytes in the filtrate was measured and compared to the unfiltered fluid. The results showed that 99.9% of the leucocytes were removed and 85% of the platelets were recovered (i.e., only 15% remained in the unfiltered fluid). For comparison, a similar test was conducted with platelet concentrate and a sample of the untreated PBT porous medium. The results showed that platelet loss for the untreated porous medium was about 50-80%. The test illustrates the ability of the GPT porous medium to pass a high proportion of the platelets during leucocyte depletion of platelet concentrate.

Test with Packed Red Cells

Packed red cells (CPD anticoagulated with AS-1 additive solution) were obtained through standard processing means. The PRC had an age of 3 days. PRC was passed through the GPT porous medium in the test housing described above under gravity head pressure at an initial flow rate of 1 cc/min. The leucocyte and platelet concentration in the filtrate was measured and compared to the unfiltered PRC. The results showed average leucocyte removal of 99.7% and an average platelet loss of 22%.

For comparison, a similar test was conducted with PRC and a sample of untreated PBT porous medium. The results showed a platelet loss of 99% for the same PBT porous medium without GPT surface modification. The test illustrates the surprising ability for the GPT porous medium to pass a high proportion of platelets contained in packed red cells.

While the invention has been described in some detail by way of illustration and example, it should be understood that the invention is susceptible to various modifications and alternative forms and is not restricted to the specific embodiments set forth. It should be understood that these specific embodiments are not intended to limit the invention, but, on the contrary, the intention is to cover all modifications, equivalents, and alternatives falling within the spirit and scope of the invention. All patents and other references cited herein are hereby incorporated by reference in their entireties as if set forth in full herein.

I claim:

1. A porous leukocyte depletion medium for removing leukocytes from a biological fluid comprising a fibrous porous medium which has been treated with a plasma generated from a mixture of gases without introducing a polymeric substance into the plasma.

2. The fibrous porous medium of claim 1 comprising synthetic fibers.

3. The porous medium of claim 1 wherein the mixture of gases includes at least one inorganic gas.

4. The porous medium of claim 3 wherein the mixture includes ammonia gas.

5. The porous medium of claim 3 wherein the mixture includes oxygen gas.

6. The porous medium of claim 1 wherein the mixture of gases includes at least one organic gas.

7. A method for the separation of leukocytes from a biological fluid comprising passing the fluid through a porous medium which has been treated with a gas plasma generated from a mixture of gases, and depleting leukocytes from the biological fluid.

8. The method of claim 7 wherein passing the biological fluid through the porous medium comprises passing the fluid through a fibrous porous medium.

9. The method of claim 8 wherein the fibrous porous medium comprises synthetic fibers.

10. The method of claim 8 wherein the biological fluid includes red cells.

11. The method of claim 8 wherein the biological fluid includes platelets.

12. The method of claim 7 wherein passing the biological fluid through the porous medium comprises passing the fluid through a medium which has been treated with a gas plasma without introducing a polymeric substance into the plasma.

13. The method of claim 7 wherein the mixture of gases includes at least one inorganic gas.

14. The method of claim 13 wherein the mixture includes ammonia gas.

15. The method of claim 7 wherein the mixture of gases includes at least one organic gas.

16. A method for processing a fluid comprising passing a gaseous fluid through a porous medium comprising a membrane which has been treated with a plasma generated from a vaporized organic material including an ethylenic monomer.

* * * * *